United States Patent
Ferrazzi

(10) Patent No.: US 8,337,390 B2
(45) Date of Patent: Dec. 25, 2012

(54) INTRACARDIAC DEVICE FOR RESTORING THE FUNCTIONAL ELASTICITY OF THE CARDIAC STRUCTURES, HOLDING TOOL FOR THE INTRACARDIAC DEVICE, AND METHOD FOR IMPLANTATION OF THE INTRACARDIAC DEVICE IN THE HEART

(75) Inventor: Paolo Ferrazzi, Bergamo (IT)

(73) Assignee: CUBE S.r.l., Massa (IT)

( * ) Notice: Subject to any disclaimer, the term of this patent is extended or adjusted under 35 U.S.C. 154(b) by 1098 days.

(21) Appl. No.: 12/219,883

(22) Filed: Jul. 30, 2008

(65) Prior Publication Data

US 2010/0030014 A1  Feb. 4, 2010

(51) Int. Cl.
*A61F 2/00* (2006.01)
(52) U.S. Cl. .......................................... 600/37
(58) Field of Classification Search .............. 600/16, 600/17, 18, 36, 37; 606/1; 128/897, 898, 128/899; 623/1.26, 2.11, 2.36; 139/50
See application file for complete search history.

(56) References Cited

U.S. PATENT DOCUMENTS

| | | | |
|---|---|---|---|
| 2,515,629 A | 7/1950 | Chambers, Jr. | |
| 3,997,923 A | 12/1976 | Possis | |
| 4,164,064 A | 8/1979 | Reavill | |
| 4,865,600 A | 9/1989 | Carpentier et al. | |
| 5,011,481 A | 4/1991 | Myers et al. | |
| 5,041,130 A | 8/1991 | Cosgrove et al. | |
| 5,674,280 A | 10/1997 | Davidson | |
| 5,776,189 A | 7/1998 | Khalid | |
| 5,961,539 A | 10/1999 | Northrup | |
| 5,984,959 A * | 11/1999 | Robertson et al. | 623/2.11 |
| 6,217,610 B1 | 4/2001 | Carpentier et al. | |
| 6,254,642 B1 * | 7/2001 | Taylor | 623/23.64 |
| 6,264,602 B1 | 7/2001 | Mortier | |
| 6,360,749 B1 | 3/2002 | Jayaraman | |
| 6,425,856 B1 | 7/2002 | Shapland et al. | |
| 7,226,477 B2 * | 6/2007 | Cox | 623/2.37 |
| 7,455,738 B2 * | 11/2008 | Patel et al. | 148/402 |
| 2003/0045929 A1 | 3/2003 | McCarthy | |
| 2003/0158570 A1 * | 8/2003 | Ferrazzi | 606/191 |

(Continued)

FOREIGN PATENT DOCUMENTS

EP  1645244  4/2006

(Continued)

OTHER PUBLICATIONS

Partial International Search Report mailed Sep. 23, 2009 in PCT/EP2009/059765.

(Continued)

*Primary Examiner* — Charles A Marmor, II
*Assistant Examiner* — Catherine E Burk
(74) *Attorney, Agent, or Firm* — Davidson Berquist Jackson & Gowdey, LLP

(57) ABSTRACT

An intracardiac device for restoring the functional elasticity of the cardiac structures, in particular for the treatment of cardiomyopathies and or valvulopathies, by storing energy from the cardiac structures and ceding energy to the cardiac structures during the cardiac cycle, has an elongated shape, is at least partially wound in coils and is attachable to a cardiac structure; the coils are selected in material, number and dimension so as to allow an elastic elongation of the intracardiac device higher than 10% of the rest length of the intracardiac device and are exposed, in use, to the blood flow.

19 Claims, 13 Drawing Sheets

U.S. PATENT DOCUMENTS

| | | | |
|---|---|---|---|
| 2004/0138745 A1 | 7/2004 | Macoviak | |
| 2005/0065601 A1 | 3/2005 | Lee | |
| 2005/0288776 A1* | 12/2005 | Shaoulian et al. | 623/2.37 |
| 2006/0004247 A1 | 1/2006 | Kute | |
| 2006/0074484 A1 | 4/2006 | Huber | |
| 2006/0184241 A1 | 8/2006 | Marquez | |
| 2006/0206203 A1* | 9/2006 | Yang et al. | 623/2.37 |
| 2006/0241748 A1* | 10/2006 | Lee et al. | 623/2.37 |
| 2007/0016289 A1 | 1/2007 | Johnson | |

FOREIGN PATENT DOCUMENTS

| | | |
|---|---|---|
| EP | 1854429 | 11/2007 |
| WO | WO 97/26829 | 7/1997 |
| WO | WO 99/49816 | 10/1999 |
| WO | WO 01/08608 | 2/2001 |
| WO | WO 04/000172 | 12/2003 |
| WO | WO 2005099374 A2 * | 10/2005 |
| WO | WO 2005/112832 | 12/2005 |
| WO | WO 2006/078694 | 7/2006 |
| WO | WO 2006/086434 | 8/2006 |

OTHER PUBLICATIONS

U.S. Appl. No. 10/257,500—Jun. 9, 2009 PTO Office Action.
International Search Report mailed Nov. 17, 2009 in PCT Appln. No. PCT/EP2009/059765.
U.S. Appl. No. 10/257,500—Nov. 12, 2009 PTO Office Action.
Ferrazzi, Paolo et al., "Implantation of an Elastic Ring at Equator of the Left Ventricle Influences Cardiac Mechanics in Experimental Acute Ventricular Dysfunction," Journal of AMerican College of Cardiology, col. 50, No. 18, 2007.
Ferrazzi, Paolo et al., "The Titan can help titin: from micro to macro myocardial elasticity," Italian Federation of Cardiology, 1558-2027, 2006.
JP Appln. No. 2001-575929 Jan. 4, 2011 JPO Office Action.

* cited by examiner

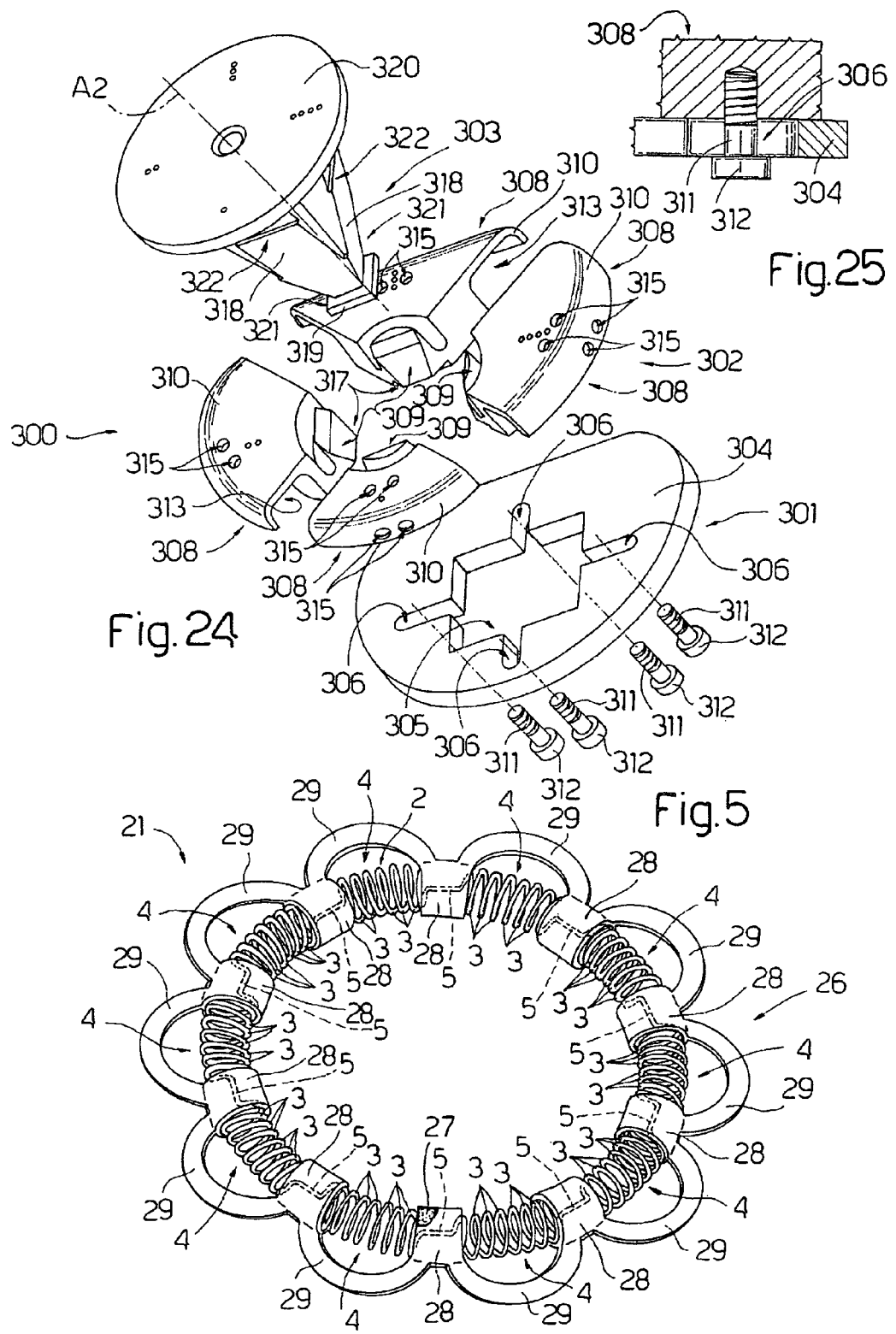

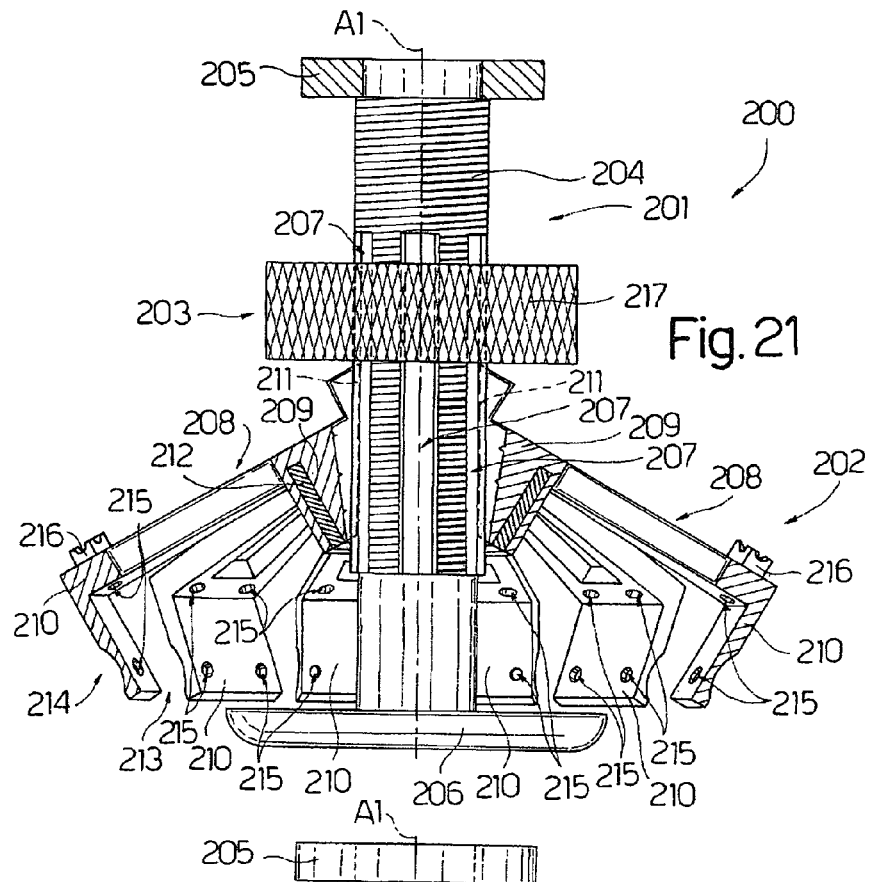
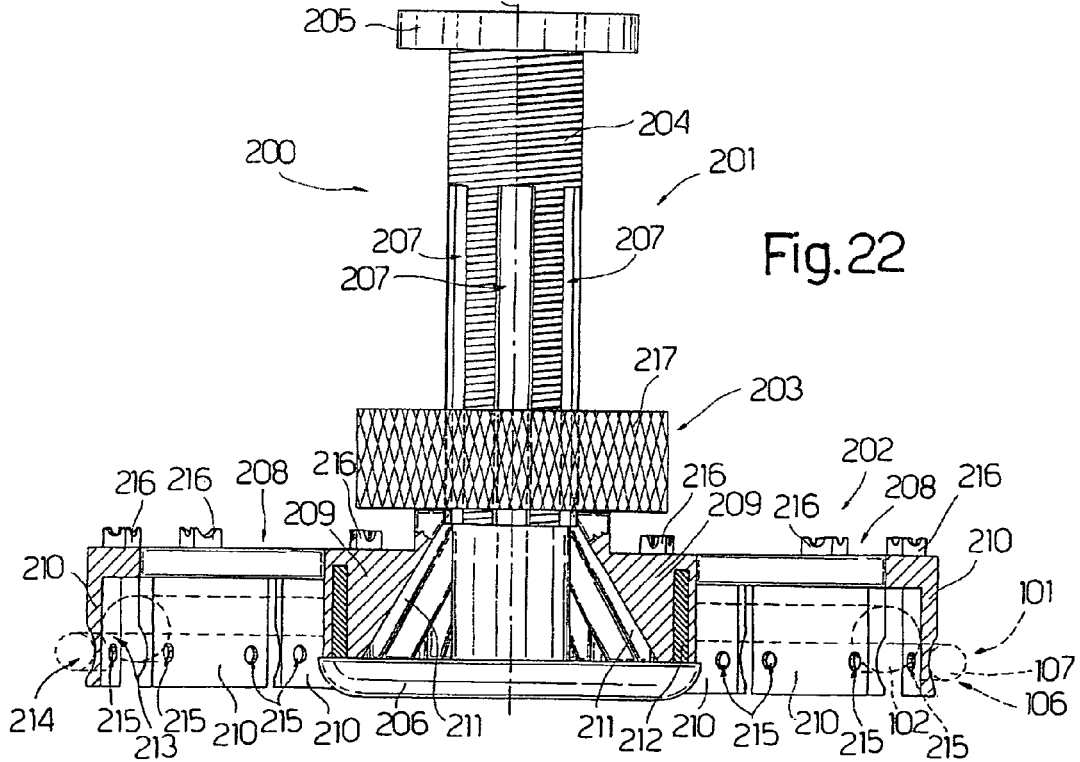

INTRACARDIAC DEVICE FOR RESTORING THE FUNCTIONAL ELASTICITY OF THE CARDIAC STRUCTURES, HOLDING TOOL FOR THE INTRACARDIAC DEVICE, AND METHOD FOR IMPLANTATION OF THE INTRACARDIAC DEVICE IN THE HEART

FIELD OF THE INVENTION

The present invention relates to an intracardiac device for restoring elasticity of cardiac structures.

In particular, the present invention relates to a device for the treatment of cardiomyopathies and valvulopathies.

BACKGROUND OF THE INVENTION

In order to better understand cardiac dysfunctions such as cardiomyopathies and valvulopathies, object of the treatment and which affect the heart, we will provide a brief description of the heart structure and function.

The heart comprises cavities which communicate with one another and with the venous and arterial system through valves. In the case in question, the heart comprises four cavities: a right atrium, a left atrium, a right ventricle, and a left ventricle; and four valves: the mitral valve, the aortic valve, the pulmonary valve and the tricuspid valve. The blood from the human body transits through the right atrium and from here crosses through the tricuspid valve, to the right ventricle which pumps the blood to the lungs through the pulmonary artery. The right ventricle is separated from the pulmonary artery by the pulmonary valve which regulates the flow. The oxygenated blood from the lungs is fed through the pulmonary veins, to the left atrium, which communicates with the left ventricle through the mitral valve. The left ventricle feeds the oxygenated blood to the human body through the aorta, from which it is separated by the aortic valve.

The pumping action of the blood is performed by the right ventricle and the left ventricle, the walls of which are defined, at least partially, by the cardiac muscle that determines in succession, the diastolic phases, in other words the dilatation phases of the right and left ventricles with relative blood filling, with intervals of systolic phases, or contraction phases of the right and left ventricles with relative expulsion of the blood from the ventricles in question.

The term heart failure defines a physiopathological state wherein the heart is not able to pump the blood in sufficient quantities for the metabolic requirements of the tissues, or wherein it performs a pumping action with excessively high filling pressure.

Heart failure can generally be determined by a dilative cardiomiopathy, in other words, a dysfunction of the cardiac muscle that reduces the efficiency of the heart in systolic phase or by a valvulopathy, in other words, affection of at least one of the cardiac valves: the mitral valve, the aortic valve, the tricuspid valve, or the pulmonary valve. In mechanical terms, the valves play a fundamental role in regulating the flow and must work in perfect synchronization with diastolic and systolic succession.

The opening and closing action of the cardiac valves is mainly determined by the pressure level upstream and downstream of the valve and by the variation induced by the ventricular walls.

The mechanical function of each component of the cardiac pump (ventricular walls, structures that comprise the valves) has a physiologically elastic behaviour, and mechanical dysfunction is caused by the loss of elasticity of these components.

Alteration to elastic properties provokes dysfunctions that are generally defined as heart failures.

The most common form of heart failure of a mechanical nature is due to the excessive dilatation (dilative cardiomiopathy) of a ventricular chamber (in particular the left chamber) that can provoke a series of geometrical changes that also alter the geometry and function of the atrioventricular valve (above all the mitral valve) making it insufficient/not competent (valvulopathy).

Problems concerning heart failure are the object of many scientific publications and many patents. As far heart failure repair at valvular level is concerned, a known method is the use of constrictor rings, among which, the most well-known is the Carpentier ring. The repair technique which uses constrictor rings has been well consolidated and particular evolution in relation to constrictor rings has been the object of many patents and patent applications, among which we recall the following: U.S. Pat. No. 5,674,280 (Davidson); U.S. Pat. No. 4,164,064 (Cooley); U.S. Pat. No. 5,776189 (Kahlid); U.S. Pat. No. 6,360,749 (Jayaraman); US 2007/0016289 (Johnson); US 2004/0138745 (Macoviak); US 2006/0074484 (Huber); WO 2006/078694 (Speziali); U.S. Pat. No. 5,961,539(Northrup); US 2006/0184241 (Marquez); WO 2006/086434 (Evalve Inc.); US 2005/0065601 (Lee); and US 2003/0045929 (McCarthy).

Other patent documents, including US 2006/081968 (Duran) suggest the insertion of mechanical devices by percutaneous intervention into the interventricular veins for the treatment of heart failure at mitral level.

Other patent documents propose solutions for heart failure caused by dilatation and dysfunction by providing constricting instruments conceived to prevent any further dilatation phenomena. These patents include U.S. Pat. No. 6,264,602 (Mortier); US 2006/0004247 (Kute).

Solutions to heart failure problems have been proposed for the treatment of both cardiomyopathies and valvulopathies which use the cardiac cycle and create an exchange of energy between the cardiac structures and the intracardiac device.

Among these solutions there is that proposed by the Applicant in the patent application WO 01/078625, wherein an intracardiac device is described, comprising an elongated member, which is elastically extendable. Basically, when the intracardiac device is implanted along the equatorial plane of the ventricular or along the valvular mitral annulus, it stores elastic energy during the diastolic phase and cedes this energy during the systolic phase to the respective cardiac structure, in this particular case, the tissues that form the walls of the ventricular or valvular annulus.

This solution is also the object of publications in the JCM Journal of Cardiovascular Medicine 2006 Vol. 1 No. 00—THE TITAN CAN HELP TITIN: FROM MICRO TO MACRO MYOCARDIAL ELASTICITY.

A further article on the same subject is published in the JACC Journal of America College of Cardiology Oct. 30, 2007 Vol. 50 No. 18 2007—IMPLANTATION OF AN ELASTIC RING AT EQUATOR OF THE LEFT VENTRICLE INFLUENCES CARDIAC MECHANICS IN EXPERIMENTAL ACUTE VENTRICULAR DYSFUNCTION.

These scientific publications endorsed the validity of the basic idea and led the Applicant to researching more deeply into the structural nature of intracardiac device and its compatibility with the human organism.

Generally, the presence of an artificial body inside a cardiac cavity always provokes a reaction by the organism, consisting of the generation of a fine layer of fibrous tissue.

Live experiments performed on sheep have shown a fibrotic reaction that in certain cases provoked attachment connection hardening, and consequential unwelcome stress on the sutures. Furthermore, an excessive fibrotic reaction could reduce elasticity and compromise correct operating function.

SUMMARY OF THE INVENTION

An object of the present invention is to minimize the tissutal reaction of the cardiac structure to a foreign body inside the heart.

Another object of the present invention is to reduce the thrombogenic capacity of the intracardiac device.

A further object of the present invention is to maintain the elastic property of the intracardiac device for a long period of time.

Another object of the present invention is to provide a cardiac device which is easy to implant.

In particular, an object of the present invention is to provide an intracardiac device which is able to minimize the efforts exchanged between the intracardiac device and the cardiac structure, and to obtain greater intracardiac device reliability levels over much longer periods of time.

Therefore, the present invention relates to an intracardiac device for restoring functional elasticity of cardiac structures, in particular for the treatment of cardiomyopathies and valvulopathies, storing energy from the cardiac structures and ceding energy to the cardiac structures during the cardiac cycle; wherein the intracardiac device has an elongated shape, and is at least partially wound in coils along a given section, and attachable to a cardiac structure; said coils being selected in material, number, and dimension to permit the elastic elongation of the intracardiac device higher than 10% of the rest length of the intracardiac device, and being exposed to blood flow during use.

The combination of the high deformation level as well as the fact of leaving the coils exposed to the blood flow, determines a high washing level by the blood flow on one hand, and the reduced probability of forming thrombosis, on the other.

Yet another object of the present invention is to provide a method for implanting the intracardiac device in a cardiac structure for the treatment of cardiomyopathies or valvulopathies which is rapid and simple to perform. A method is provided according to the present invention for implanting an intracardiac device in the heart for restoring functional elasticity of cardiac structures, in particular for the treatment of cardiomyopathies and valvulopathies, storing energy from the cardiac structures and ceding energy to the cardiac structures during the cardiac cycle; wherein the intracardiac device has an elongated shape and is at least partially wound in coils along a given section and is attachable to a cardiac structure; said coils being selected in material, number, and dimension to permit elastic elongation of the intracardiac device higher than 10% of the rest length of the intracardiac device, and being exposed to blood flow during use; the method also includes the phases of arranging the intracardiac device in an extended configuration in relation to the rest configuration; and attaching the intracardiac device in the extended configuration along an internal face of a cardiac structure.

Another object of the present invention is to provide a holding tool for an intracardiac device that acts as an auxiliary during the implant phase of the intracardiac device.

A holding tool is also provided according to the present invention, for an intracardiac device in the heart for restoring functional elasticity of cardiac structures, in particular for the treatment of cardiomyopathies and valvulopathies, storing energy from cardiac structures and ceding energy to the cardiac structures during the cardiac cycle; wherein the device has an elongated shape and is at least partially wound in coils along a given section and attachable to a cardiac wall; the said coils being selected in material, number, and dimension to permit elastic elongation of the intracardiac device higher than 10% of the rest length of the intracardiac device; the support tool comprises a holding unit having a variable configuration in a manner so that it supports the intracardiac device in the rest configuration and in an extended configuration in relation to the rest configuration.

BRIEF DESCRIPTION OF THE DRAWINGS

Further characteristics and advantages of the present invention will appear more clearly from the following description of non-limiting examples of embodiments, with reference to the figures in the appended drawings, wherein.

Figures 11A, 11B:
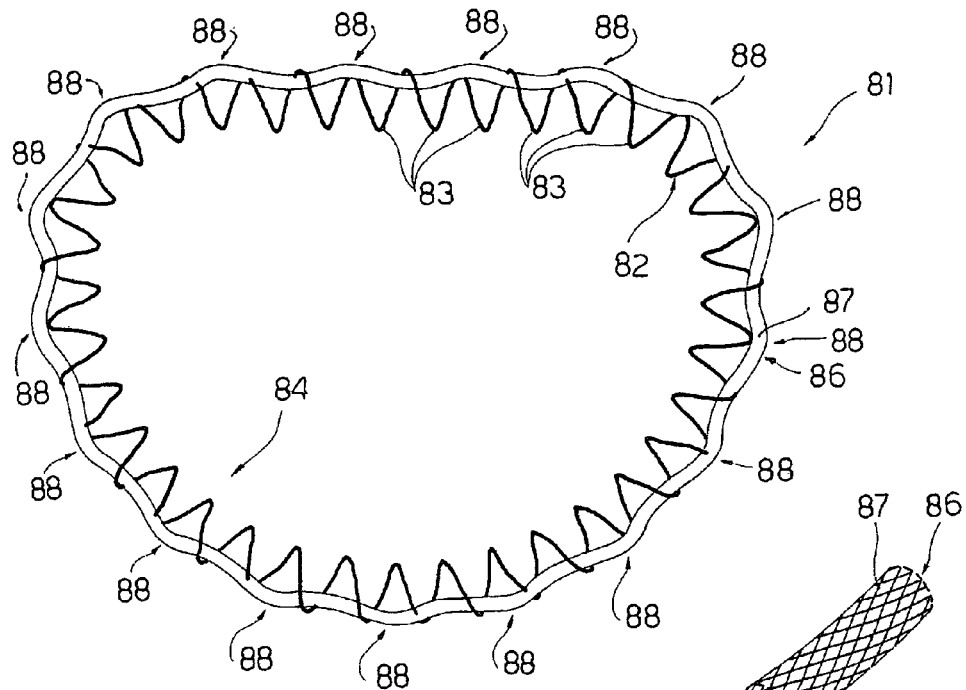
Figures 12A, 12B:
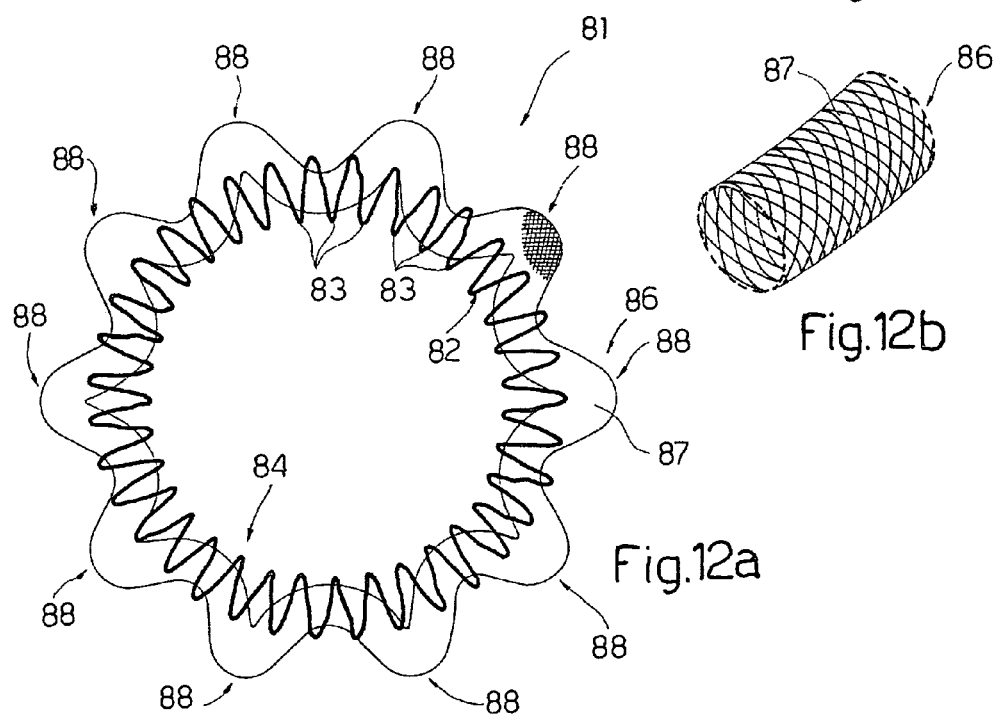
Figure 13:
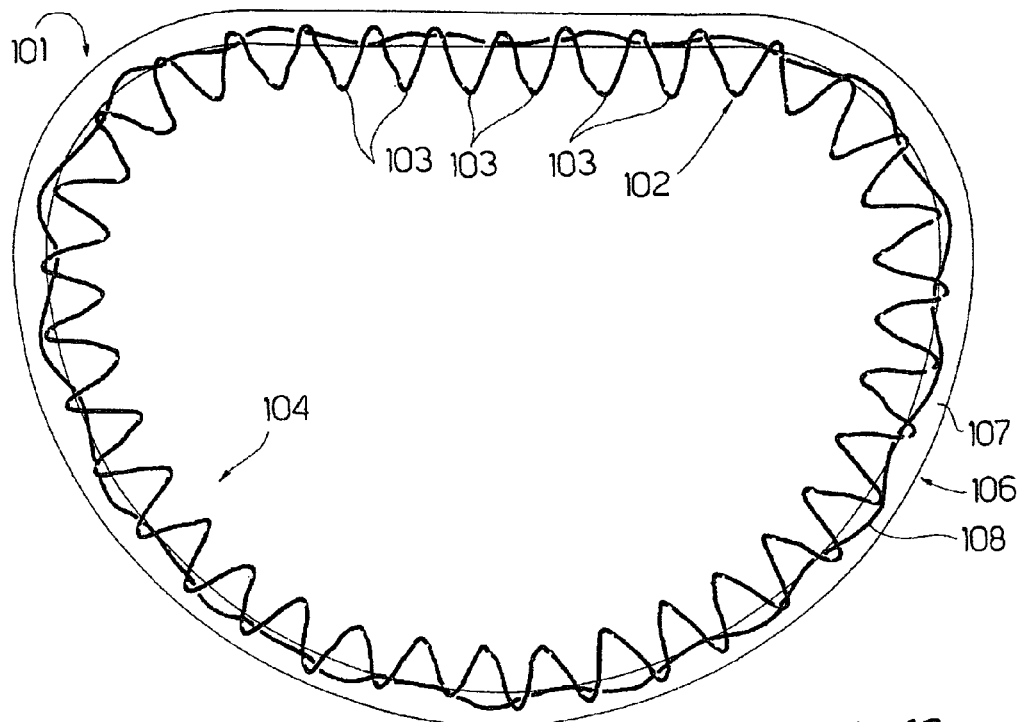
Figure 14:
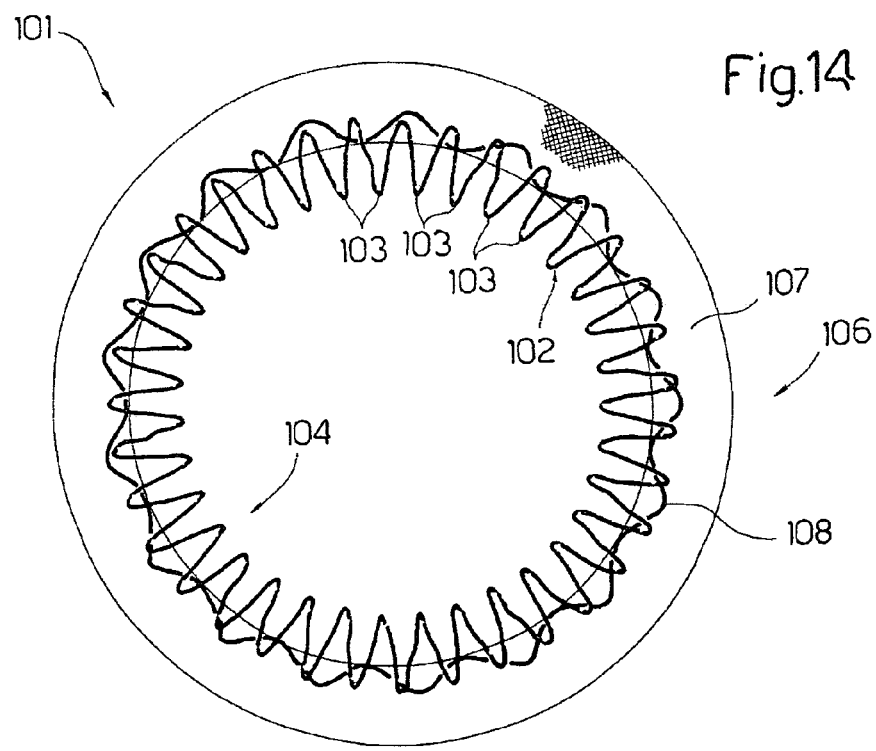
Figure 15:
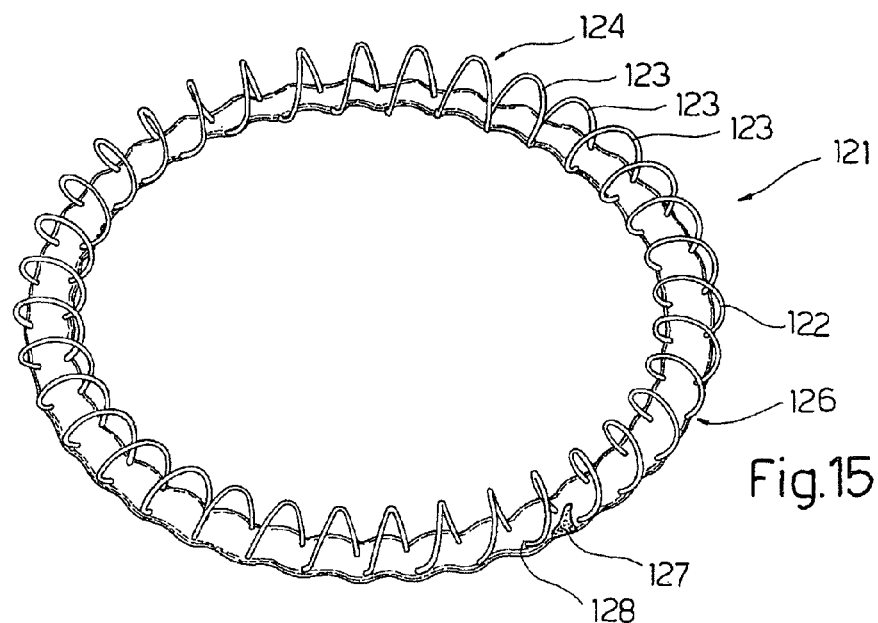
Figure 16:
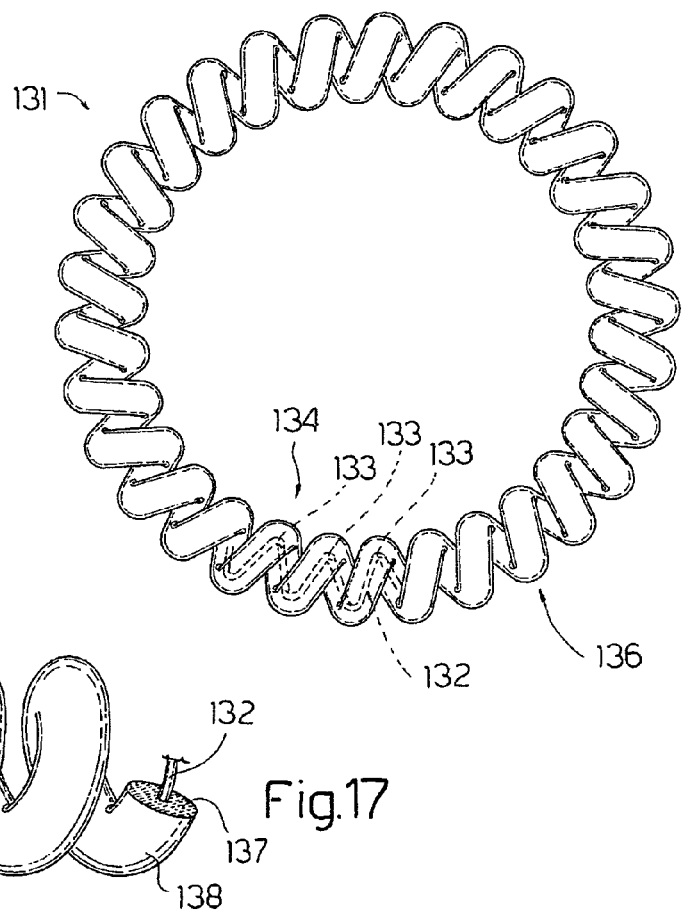
Figure 17:
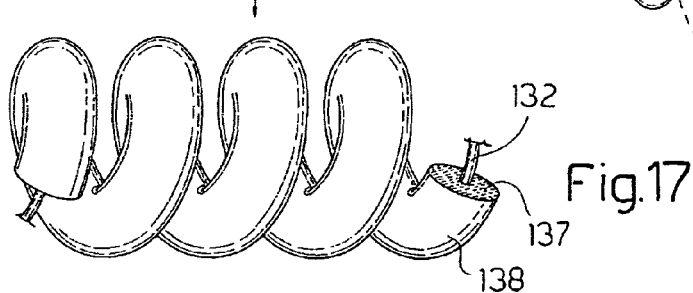
Figure 18:
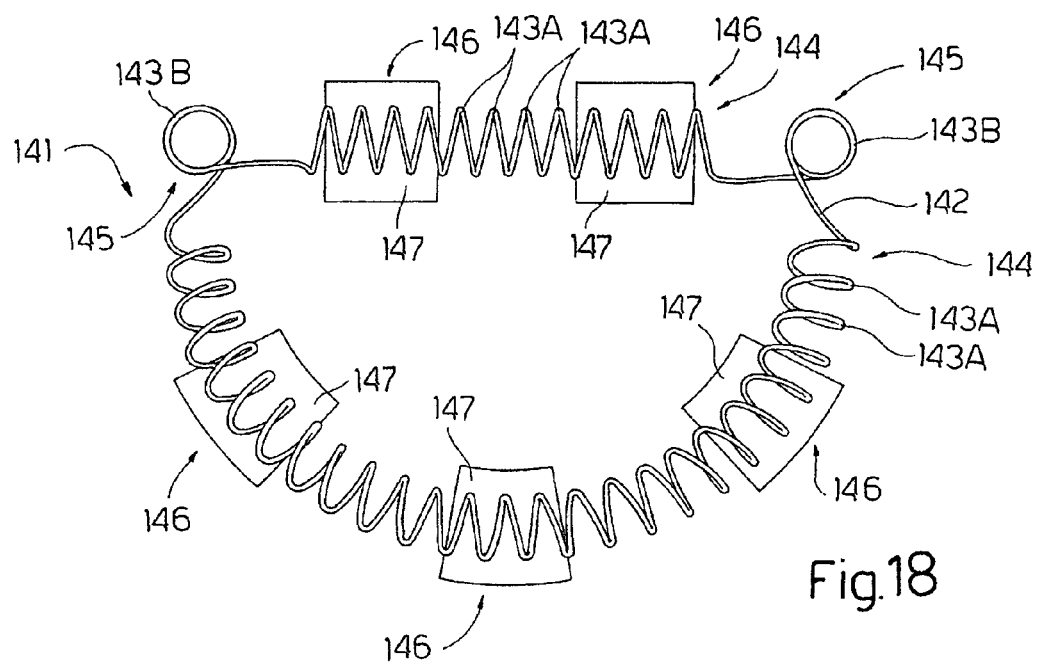
Figure 19:
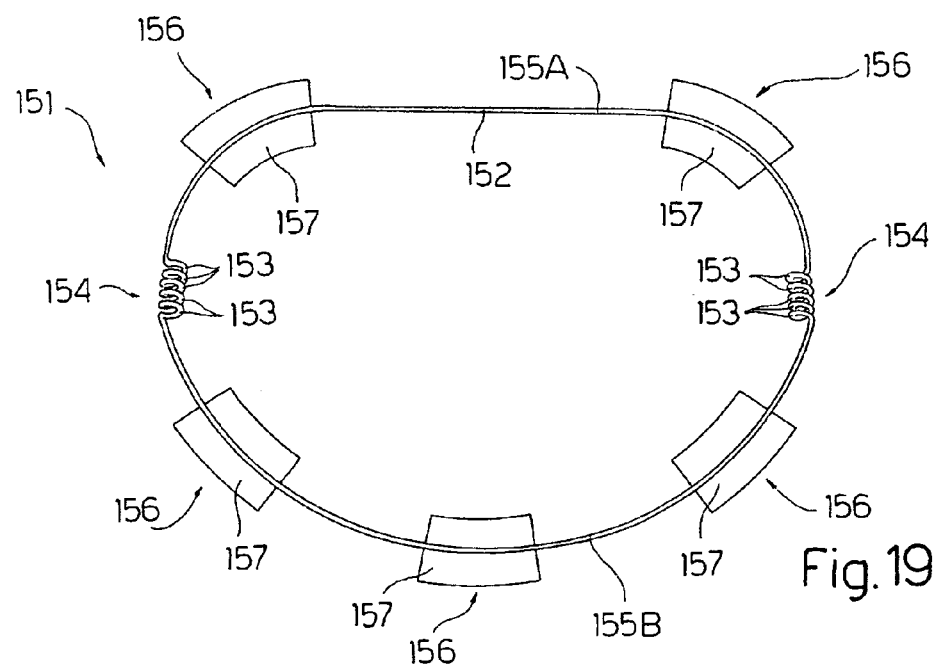
Figure 20:
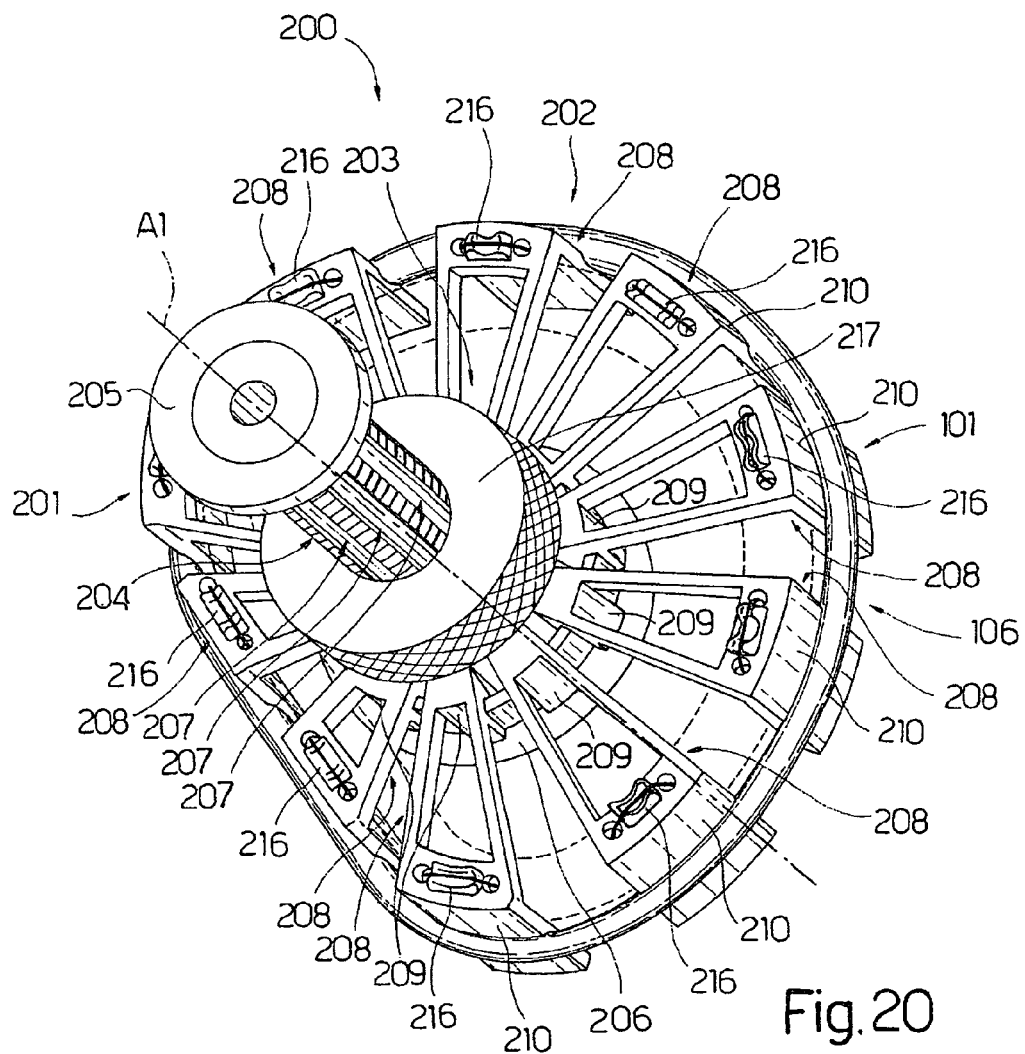
Figure 23:
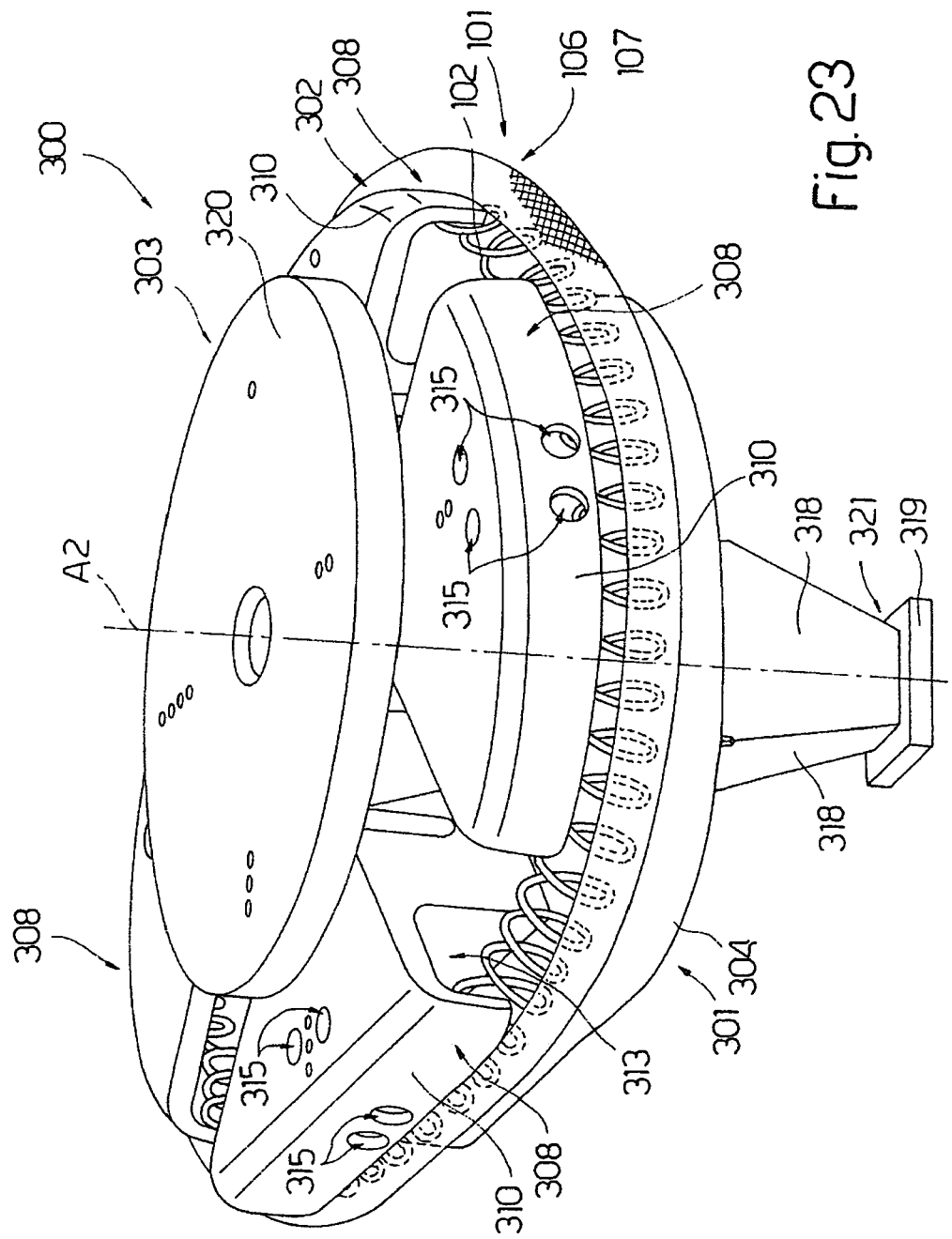

FIGS. from 5 to 10 are views in perspective of respective embodiments of the intracardiac devices according to the present invention;

FIGS. 11a and 12a are plane views of an embodiment of the intracardiac device in an extended configuration and in a rest configuration, respectively;

FIGS. 11b and 12b are views, in enlarged scale, of a detail shown in FIGS. 11a and 12a;

FIGS. 13 and 14 are plane views of a further embodiment of the intracardiac device in an extended configuration and in a rest configuration, respectively;

FIGS. 15 and 16 are views of respective embodiments of intracardiac devices according to the present invention;

FIG. 17 is a view in enlarged scale of a detail of the intracardiac device shown in FIG. 16;

FIGS. 18 and 19 are plane views of respective embodiments of intracardiac devices according to the present invention FIG. 20 is a view in perspective of a holding tool of the intracardiac device of the present invention according to a first embodiment;

FIGS. 21 and 22 are cross section views of the tool shown in FIG. 20 in two operational positions;

FIG. 23 is a view in perspective of a holding tool of the intracardiac device of the present invention according to a second embodiment;

FIG. 24 is a blow-up view in reduced scale of the tool shown in FIG. 23; and

FIG. 25 is a cross section view of a detail of the tool shown in FIG. 24.

DESCRIPTION OF THE PREFERRED EMBODIMENTS

The Heart and the Cardiac Structures

Figure 1:
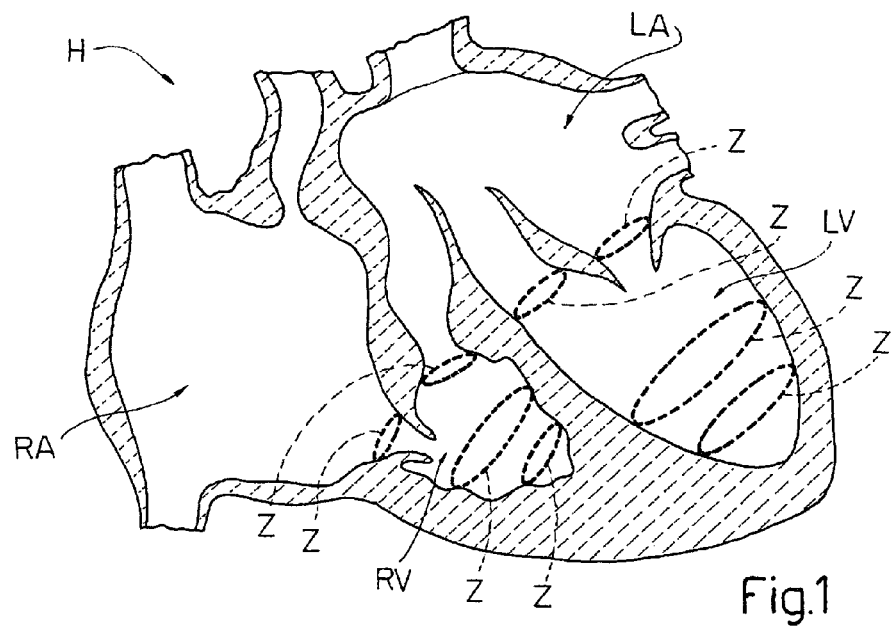
FIG. 1 is a cross section view of the heart, with certain parts removed for reasons of clarity, and wherein the zones are shown for possible implantation of the device object of the present invention.

With reference to FIG. 1, H refers to a heart comprising four chambers: a left ventricle LV, a left atrium LA, a right ventricle RV, and a right atrium RA; four valves: mitral valve, aortic valve; tricuspid valve; and pulmonary valve.

Each ventricle is defined by a wall which expands and contracts to perform the pumping action, and each valve comprises an annulus.

In the present description, the term cardiac structure refers to both the ventricular walls and the valve annuli.

The dashed lines in FIG. 1 show the zones, Z, for possible connection of an intracardiac device object of the present invention, conceived for restoring cardiac structure function, should this result as not sufficient to completely perform the function for which it is conceived. Naturally, it is obvious that the zones Z shown herein are indicative and that the intracardiac devices can be implanted in zones other than those illustrated.

It is also obvious that each zone Z requires an intracardiac device of an appropriate size adequate for the dimensions of the zone Z in question.

The following description will illustrate in greater detail various embodiments of intracardiac devices for the treatment of heart failure and conceived to be realised in different dimensions and shapes for implanting in a cardiac cavity and connected to a cardiac structure in the zones Z.

The Intracardiac Device

Figure 2:
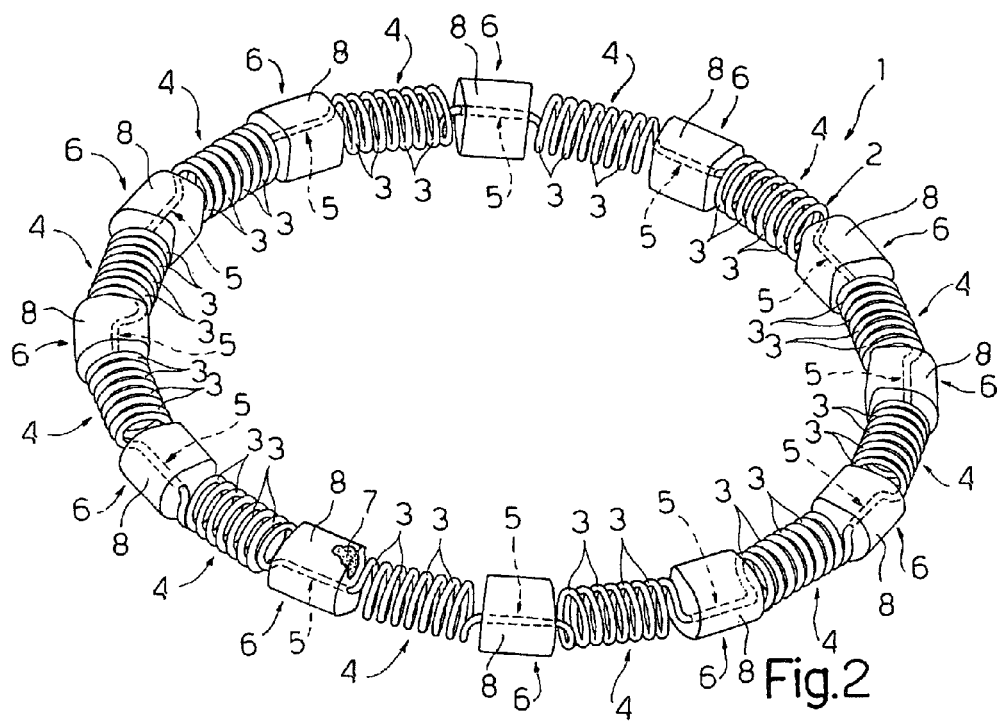
FIGS. 2, 3 are views in perspective of respective embodiments of intracardiac devices according to the present invention.

In FIG. 2, reference numeral 1 refers to an intracardiac device, having an elongated closed ring shape and comprising an elongated member 2 forming a closed ring, and members 6 attachable to the cardiac structure and attached to the elongated member 2.

In the case of FIG. 2, the elongated member 2 is defined by a metal wire, in the form of a closed ring and wound in coils 3 around sections uniformly distributed along the ring to form a plurality of cylindrical helical springs 4 in said sections. The cylindrical helical springs 4 are united by substantially straight sections 5 of metal wire. Each section 5 of metal wire is encased in a respective attachable member 6, which comprises a pad 7, preferably made of some deformable material, and a covering 8 in a biocompatible woven material, and easily attachable, such as Dacron® or Goretex®, for example, wound around pad 7.

Figure 3:
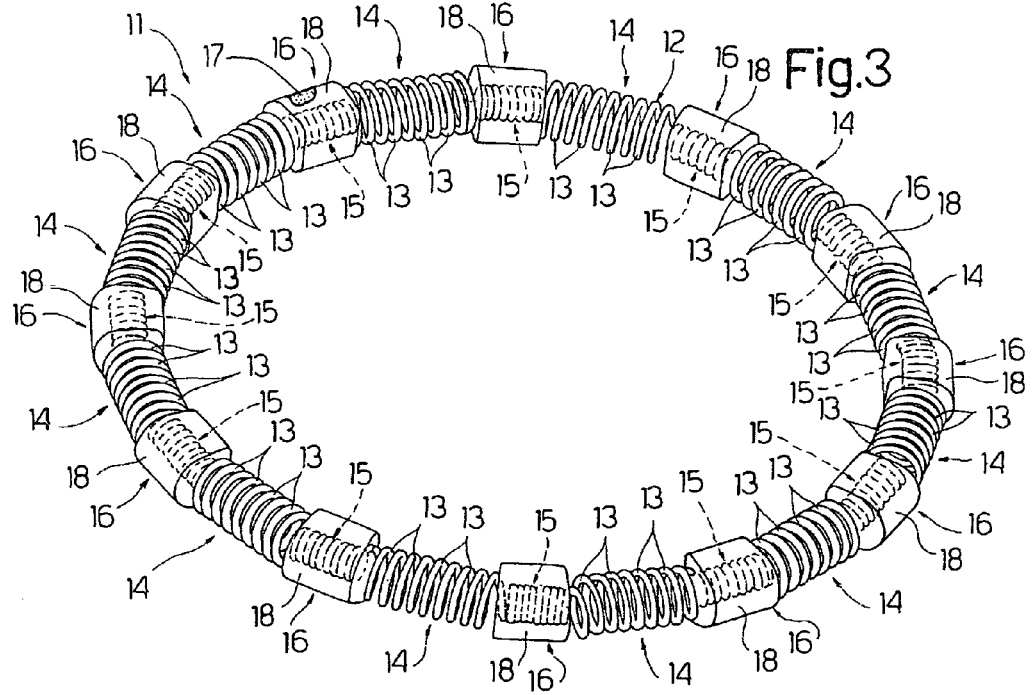
Figure 4:
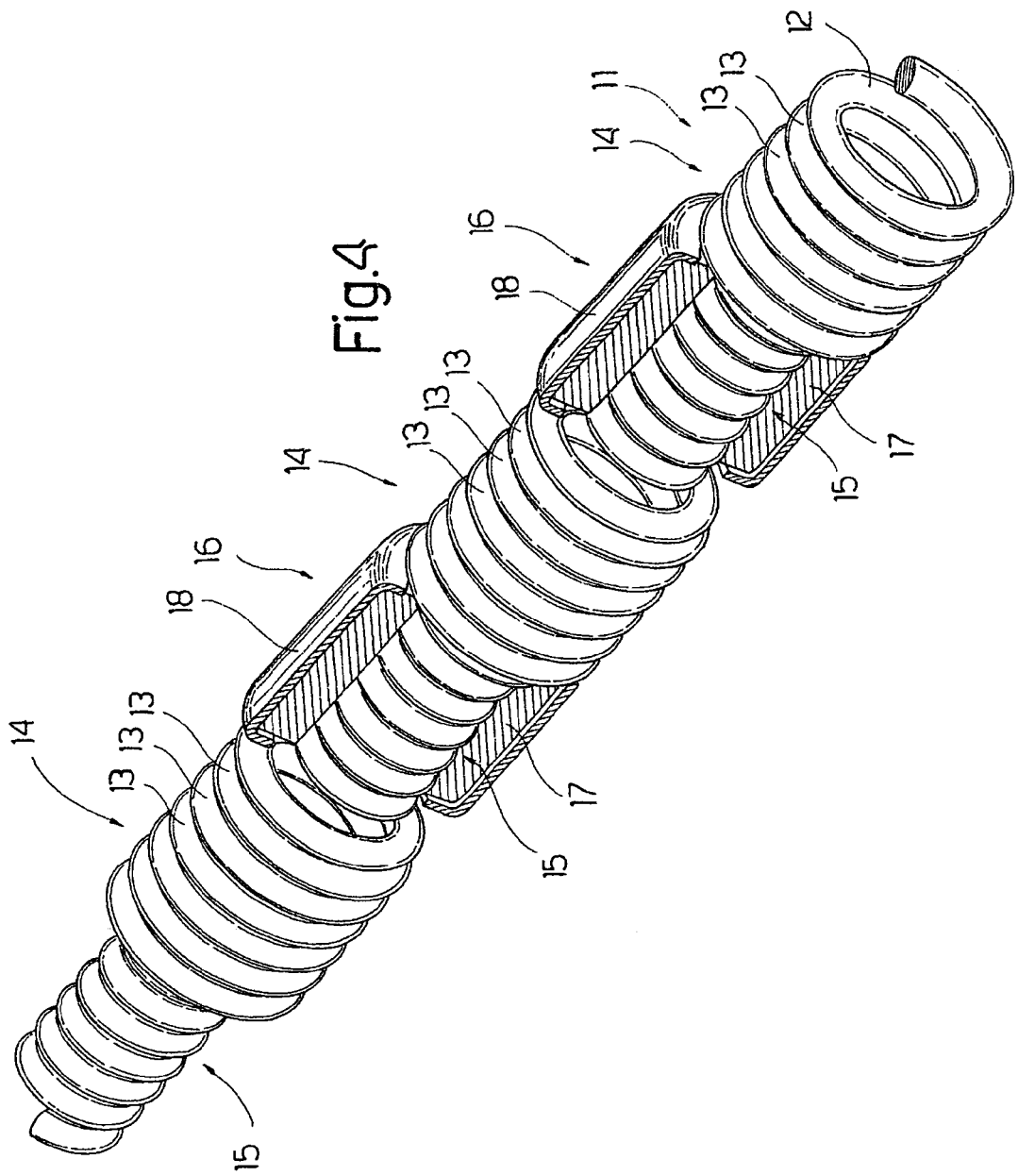
FIG. 4 is a view in perspective in enlarged scale of a detail of the intracardiac device shown in FIG. 3.

The intracardiac device 11 in FIG. 3 is a variant of the intracardiac device shown in FIG. 2 and has an elongated closed ring shape and comprises an elongated member 12 and members 16 attachable to the cardiac structure and attached to the elongated member 12. The elongated member 12 is defined by a metal wire, forming a closed ring and wound in coils 13 in sections uniformly distributed along the ring to form a plurality of cylindrical helical springs 14 in said sections and wound in a spiral around further sections to form cylindrical helical springs 15 set between the cylindrical helical springs 14. The helical springs 15 have a diameter smaller than the helical springs 14. As can be seen more clearly in FIG. 4, each helical spring 15 is encased in a respective attachable member 16, composed of a pad 17, preferably made in some deformable material, that encloses the helical spring 15, and a covering 18 in a biocompatible woven material, and easily attachable, such as Dacron® or Goretex®, for example, wound around pad 17.

In FIG. 5, the reference numeral 21 refers to an intracardiac device, having an elongated closed ring shape and comprising an elongated member 2 as described in reference to FIG. 2, and an member 26 attachable to the cardiac structure and attached to the elongated member 2.

The attachable member 26 comprises a plurality of pads 27, preferably in some deformable material; a plurality of coverings 28 in a biocompatible woven material such as Dacron® or Goretex®, easily attachable, wound around the respective pads 27; and a plurality of bands 29 of biocompatible woven material, such as Dacron® or Goretex® for example.

Each band 29 attaches two adjacent coverings 28 and extends alongside the helical spring 4. When the helical spring 4 is in the rest configuration the respective band 29 is slack, while the band 29 limits the extension of the respective helical spring 4.

Figure 6:
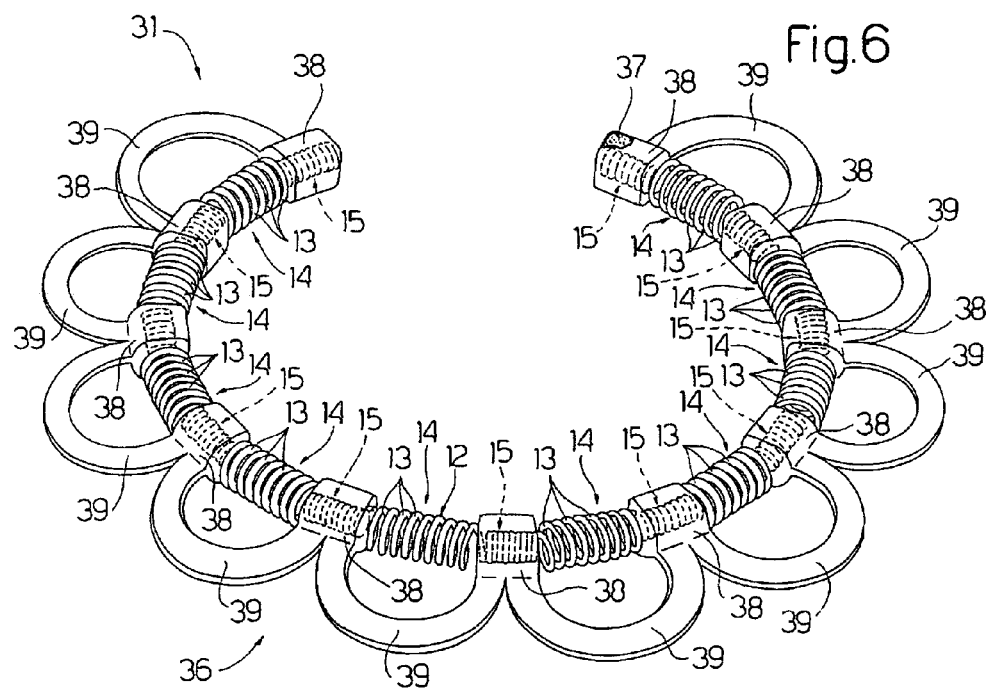

In FIG. 6, reference numeral 31 refers to an intracardiac device, having a closed ring elongated shape and comprising an elongated member 12 as described in reference to FIG. 3, but with the difference that in this case the elongated member 12 forms an open ring, and an member 36 attachable to the cardiac structure and attached to the elongated member 12.

The attachable member 36 comprises a plurality of pads 37, preferably in Goretex®; a plurality of coverings 38 in a biocompatible woven material and encasing respective helical springs 15, in Dacron® or Goretex®, for example, and easily attachable, wound around the respective pads 37; and a plurality of bands 39 in a biocompatible woven material, easily attachable, such as Dacron® or Goretex®, for example.

Each band 39 attaches two adjacent coverings 38 and extends alongside the helical spring 14. When the helical spring 14 is in the rest configuration the respective band 39 is slack, while the band 39 limits the extension of the respective helical spring 14.

Figure 7:
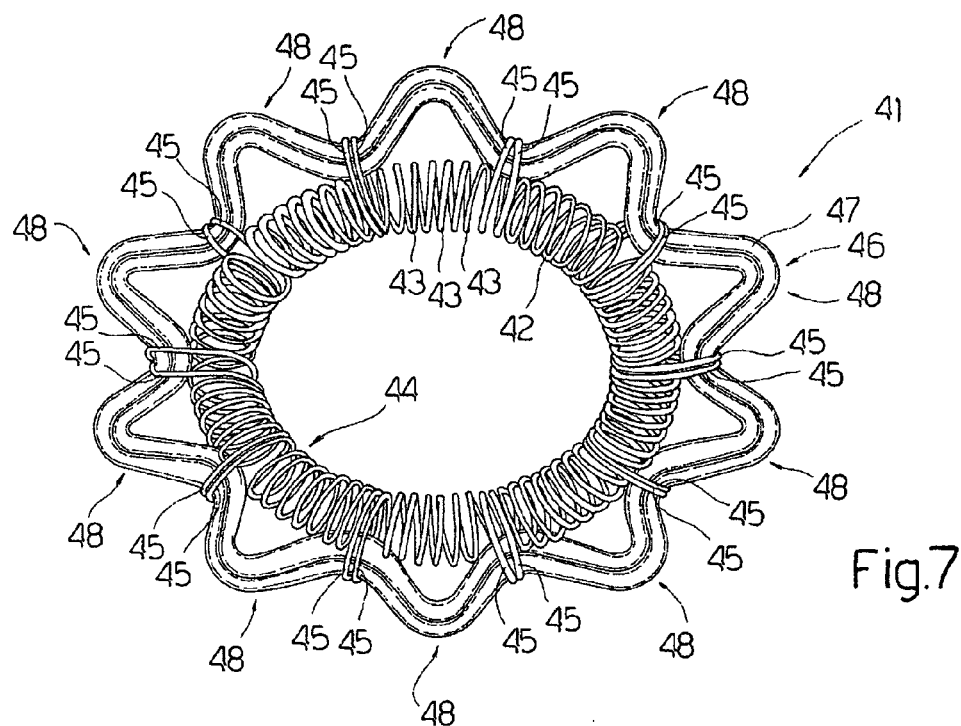

In FIG. 7, reference numeral 41 refers throughout to an intracardiac device, having an elongated closed ring shape and comprising an elongated member 42 and an member 46 attachable to the cardiac structure and attached to the elongated member 42.

The elongated member 42 is defined by a metal wire wound in a spiral to form a plurality of coils 43 set at a distance from one another to form a cylindrical helical spring 44 and pairs of adjacent coils 45 alternating with groups of coils 43. Each coil 45 presents an elongated shape in a radial direction. Furthermore, the pairs of coils 45 are uniformly distributed along the ring formed by the elongated member 42.

The attachable member 46 comprises a closed ring tubular band 47 which passes inside the coils 45 and has a length that is greater than the circumference of the helical spring 44 in the rest configuration and is arranged to form bends 48 between two pairs of adjacent coils 45.

Figure 8:
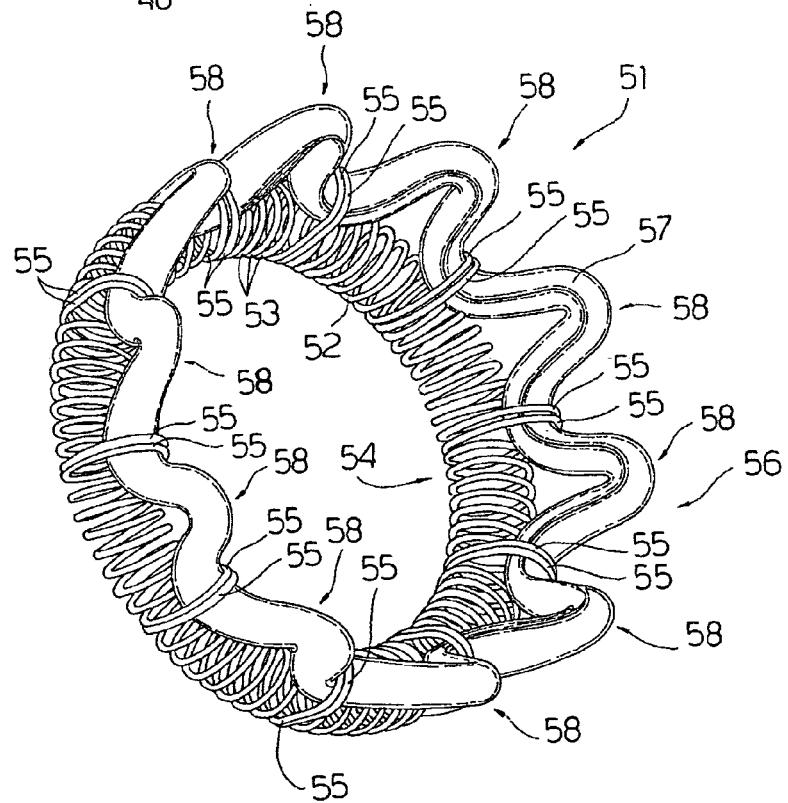

In FIG. 8, reference numeral 51 refers throughout to an intracardiac device, having an elongated closed ring shape and comprising an elongated member 52 and an member 56 attachable to the cardiac structure and attached to the elongated member 52.

The elongated member 52 is defined by a metal wire wound in a spiral to form a plurality of coils 53 set at a distance from one another to form a cylindrical helical spring 54 and pairs of adjacent coils 55 alternating with groups of coils 53. Each coil 55 has an elongated shape in an axial direction. Furthermore, the pairs of coils 55 are uniformly distributed along the ring formed by the elongated member 52.

The attachable member 56 comprises a closed ring tubular band 57 and passes inside the coils 55 and has a length greater than the circumference of the helical spring 54 in the rest configuration and is arranged to form bends 58 between the pairs of adjacent coils 55, in particular, a bend 58 between two pairs of adjacent coils 55.

Figure 9:
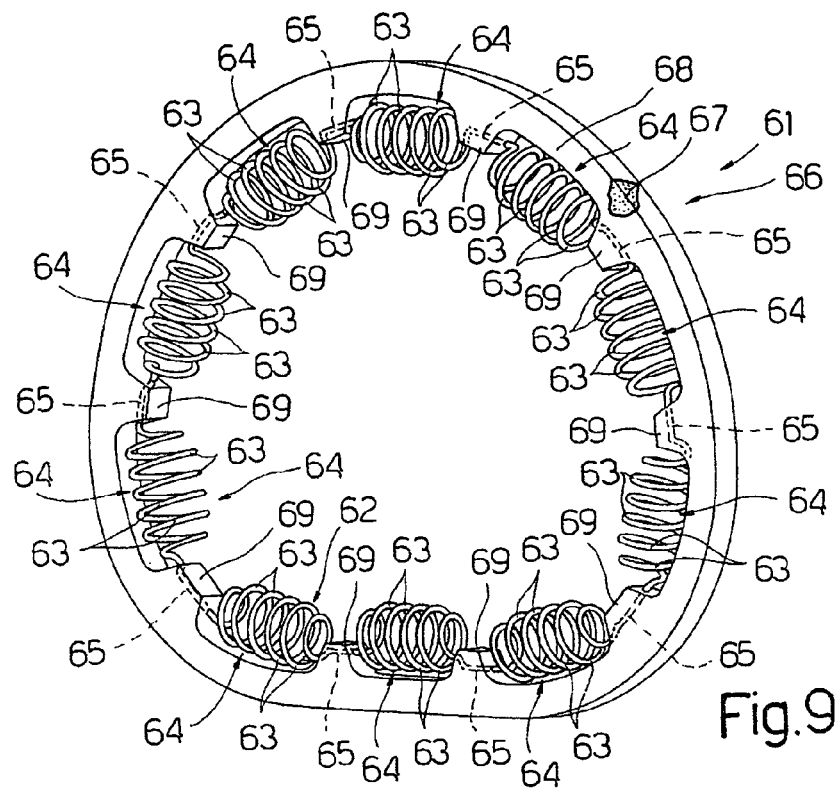

The intracardiac device 61 shown in FIG. 9 has an elongated closed ring shape and comprises an elongated member 62 and an member 66 attachable to the cardiac structure and attached to the elongated member 62.

The elongated member 62 is defined by closed ring metal wire and is wound in a spiral to form a plurality of coils 63 set at a distance from one another to form a plurality of barrel-shaped helical springs 64 and straight sections 65 alternating with the helical springs 64.

The attachable member 66 extends along a closed ring arranged externally to the elongated member 62 and comprises a ring-shaped pad 67 covered with a covering 68 and presenting lobes 69 which extend towards the interior of the ring, and which respectively encase wire sections 65.

Figure 10:
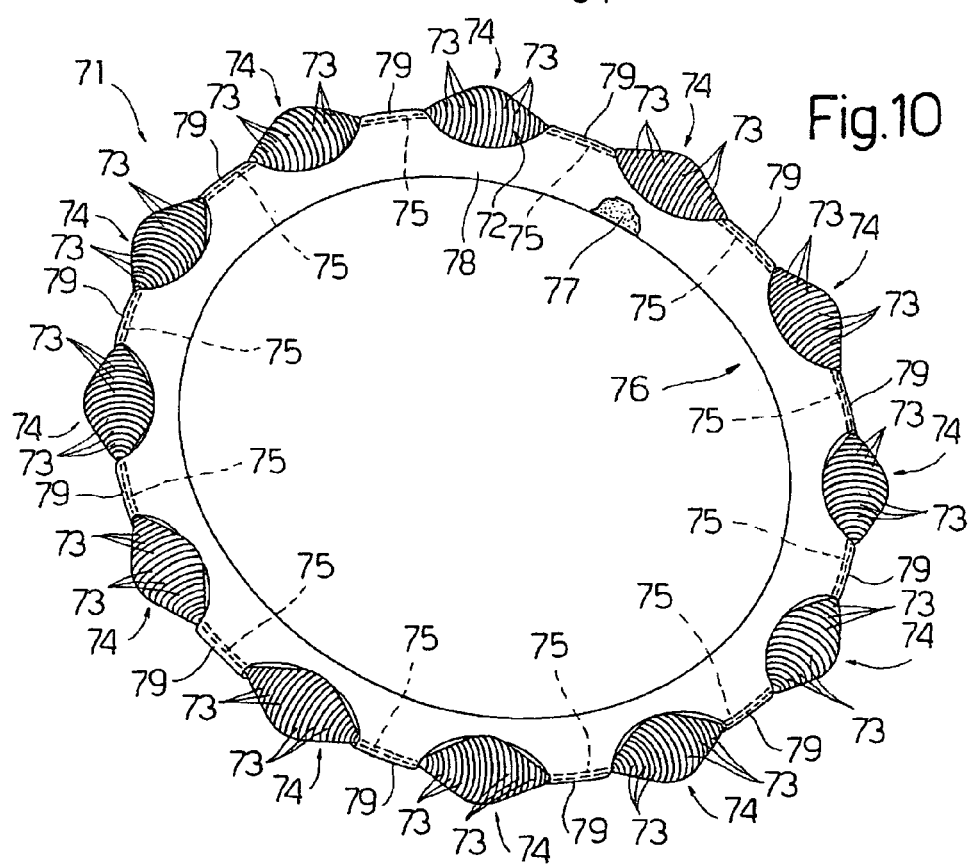

The intracardiac device 71 shown in FIG. 10 has an elongated closed ring shape and comprises an elongated member 72 and an member 76 attachable to the cardiac structure and attached to the elongated member 72.

The elongated member 72 is defined by a closed ring metal wire and is partially wound in a spiral to form a plurality of coils 73 set at a distance from one another to form a plurality of spindle-shaped helical springs 74 and straight sections 75 alternating with the helical springs 74.

The attachable member 76 is a closed ring elongated member and arranged inside the elongated member 72 and comprises a pad 77 also in closed ring shape and covered with a covering 78, and presenting lobes 79 which extend towards the exterior and encase the respective wire sections 75.

The intracardiac device 81 shown in FIGS. 11a and 12a has an elongated closed ring shape and comprises an elongated member 82 and an member 86 attachable to the cardiac structure and attached to the elongated member 82.

The elongated member 82 is defined by a closed ring metal wire and wound in a spiral to form a plurality of coils 83 set at a distance from one another to form a cylindrical helical spring 84.

The attachable member 86 comprises a closed ring tube 87 (FIG. 12b) realised in metal mesh. The tube 87 is interconnected with the coils 83 and forms bends 88. When the intracardiac device 81 is arranged in its extended configuration the tube 87 is reduced in diameter (FIGS. 11b, 12b) progressively, and the bends 88 assume a wider curved shape (FIGS. 11a and 12a), FIGS. 13 and 14 show an intracardiac device 101, comprising an elongated member 102 wound in coils 103 to form a helical spring 104 and attached to a attachable member 106 comprising a metal mesh tube 107. The intracardiac device 101 also comprises a metal wire 108 interlaced with some of the coils 103. The metal mesh tube 107 has the characteristic of being extendable for a certain length thanks to the mesh type and weave. Elongation of the tube 107 provokes a flattening action on the tube. FIG. 14 shows the intracardiac device in the rest configuration wherein the tube 107 is shown in the rest configuration.

FIG. 15 shows a closed ring intracardiac device 121, comprising an elongated member 122 and an attachable member 126. The elongated member 122 comprises a closed ring metal wire wound in a spiral to form a plurality of coils 123 set at equal distances from each other and a cylindrical helical spring 124.

The attachable member 126 forms a closed ring and comprises a silicone pad 127 or some other closed ring deformable material wherein the coils 123 are partially embedded, and a covering 128 which covers the pad 127 completely.

FIG. 16, shows a closed ring, helically wound intracardiac device 131.

The intracardiac device 131 comprises a core defined by an elongated member 132, in a closed ring, helically wound to form a plurality of coils 133 set at equal distances from each other and a cylindrical helical spring 134. As shown more clearly in FIG. 17, the intracardiac device 131 comprises an attachable member 136, that forms a pad 137 uniformly covering the elongated member 132 and a covering 138 in an attachable material that covers the pad 137 completely.

In FIG. 18, a closed ring intracardiac device 141 comprises an elongated member 142 and a number of attachable members 146. The elongated member 142 comprises a closed ring metal wire and is partially helically wound to form coils 143A divided into two helical springs 144 and two torsion springs 145 each of which being defined by a single coil 143B.

Each attachable member 146 comprises a patch 147 of attachable material wound around the elongated member 142.

In FIG. 19, a closed ring intracardiac device 151 comprises an elongated member 152 and a number of attachable members 156. The elongated member 152 comprises a closed ring metal wire and is partially helically wound to form coils 153 divided into two helical springs 154, which are connected to each other by two sections 155A and 155B and extending for a length that is much greater than the length of the springs 154.

Each attachable member 156 comprises a patch 157 of attachable material wound and attachable at least partially around the elongated member 152, in particular attachable to the sections 155A and 155B.

The intracardiac devices 1, 11, 21, 31, 41, 51, 61, 71, 81, 101, 121, 131, 141, and 151 described, have certain characteristics in common, in particular, they are able to correct cardiomyopathies and valvulopathies, storing energy from the cardiac structures and ceding energy to the cardiac structures during the cardiac cycle, they have an elongated shape, and are, at least partially wound in coils along a given section, and are attachable to a cardiac structure. Furthermore, the coils are selected for their material, number, and dimension to permit elastic elongation of the intracardiac device higher than 10% of the rest length of the intracardiac device, and are exposed to blood flow during use.

The exposure of the coils to the blood flow provides a washing action on the device coils and the reduction of thrombogenicity.

The coils are selected in material, number and dimension, according to the type of application and the implantation zone of the intracardiac device, to permit elastic elongation of the intracardiac device between 10% and 50% of the rest length of the intracardiac device. Valvular type implantations require more reduced deformation, while ventricular applications at equatorial level require extension longer than 10% and closer to 50% of the rest length of the intracardiac device.

Furthermore, the coils are selected according to material, number and dimension to permit elastic shortening in relation to the rest length of the intracardiac device lesser than 5% of the rest length of the intracardiac device in order to permit an accumulation of elastic energy even during the terminal systolic phase.

In rest configuration the coils are set at a distance from one another to permit elastic compression of the device as well as elastic traction.

Each elongated member is realised using metal wire for springs, which is at least partially wound in coils to form one or more springs arranged in succession.

The intracardiac device comprises at least one member directly attachable to the cardiac structure attached to the elongated member in a manner to leave the coils exposed to blood flow at least partially during use.

Furthermore, in certain embodiments the attachable member 26, 36, 46, 56, 66, 76, 86, 106, 126, 136 has an elongated shape and is arranged alongside and along the elongated member and is extendable within a maximum length in order to limit extension of the elongated member within a percentage determined by the rest length of the elongated member.

In other embodiments the function of limiting the maximum extension of the intracardiac device is performed by a metal wire 108 (FIGS. 13 and 14).

The metal mesh tubes 87, and 107 of the intracardiac devices 81, and 101 shown in FIGS. 11a-14 are particularly interesting, because the metal mesh tubes 87, and 107 are extendable, and once they have been extended, the diameter of the metal mesh tubes 87 and 107 is reduced, and therefore they occupy less space, are resistant, biocompatible, and easily attachable.

The attachable member comprises a support structure realised in a material selected from one of the following:
Metal;
Silicone;
Polyurethane;
Dacron®;
Goretex®;
and possibly also a covering of attachable material. This covering is realised in a material selected from one of the following:
Dacron®
Goretex®
Pericardial material
Metal.

The attachable member associated with the elongated member is conceived to maintain the elongated member at an adequate distance from the face of the cardiac structure, preventing, or at least reducing the amount of coil rubbing against the cardiac wall during extension and compression phases of the intracardiac device 1. Furthermore, the space between the coils and the cardiac wall facilitates the passage of the blood between the coils, and therefore also the "washing" action by the blood which minimizes the formation of platelet aggregates which could compromise the elasticity of the elongated member provoking thrombosis.

The attachable member separated from the elongated member also allows the intracardiac device to be attached in a more efficient manner to optimize the effort exchanged between the elongated member and the cardiac structure. Separately from the structure of the elongated member, the attachable member, in particular the continuous type attachable member permits the distribution of the efforts exchanged between the cardiac wall and the elongated member.

Where the pads in deformable material have been described, variants (not illustrated) are also foreseen, wherein the pads are omitted and the covering is wound directly around the elongated member Intracardiac Device Support Instrument In FIG. 20, reference numeral 200 refers to a holding tool of the intracardiac device and which acts as an auxiliary for implantation of the intracardiac device in the heart H (FIG. 1), in the case of the intracardiac device 101 illustrated in FIG. 13. The tool 200 extends along an axis A1 and comprises a frame 201, a holding unit 202 of the intracardiac device 101; and a driving member 203 conceived to drive and maintain the holding unit 202 in various operational positions.

In FIGS. 21 and 22 the frame 201 is defined by a threaded bar 204 on axis A1 and by two plates 205 and 206 fixed to opposite ends of the bar 204. As well as being threaded, the bar 204 also has grooves 207 parallel to the axis A1.

The holding unit 202 extends around the bar 204 and comprises a plurality of arms 208, each one having a hub portion 209 partially engaged in a groove 207 and a holding portion 210. The hub portion 209 is attached in the groove with a rib 211 on a slope in relation to the arm 208 in a manner, so that when the rib 211 is parallel to the axis A1 the arm 208 is on a slope in relation to the axis A1.

The arms 208 are connected to one another by an elastic band 212, which basically maintains the arms 208 in the position which minimizes the elastic force of the elastic band 212 in question, in other words, with the ribs 211 arranged parallel to the axis A1 (FIG. 21).

In FIG. 22, the holding portion 210 defines an inner seat 213 to house the elongated member 102 and an outer seat 214 to house the attachable member 106.

It is obvious that the holding portion 210 can be modified according to the type of intracardiac device and with the specific function of leaving the attachable member 106 exposed as far as possible.

The holding portion 210 has holes 215 and bridges 216 for the suture thread conceived to fix the intracardiac device 101 to the holding portion 210.

The driving member 203 comprises a ring 217 with a hole internally threaded and coupled with the bar 204.

As shown in FIGS. 21 and 22, the screwing action of the driving member 203 on the bar 204 determines the approach of the driving member 203 towards the plate 206 and progressively pushes the holding unit 202 against the plate 206. In other words, the arms 208 are held tightly between the plate 206 and the driving member 203 and, in this manner, resist against the force of the elastic band 212, and are arranged radially in relation to the axis A1. Consequently, the intracardiac device 101 is extended from a rest configuration to an extended configuration as shown in FIG. 22.

The tool 200 is characterised in that it is able to arrange the intracardiac device 101 in a plurality of intermediate configurations in relation to those illustrated in FIGS. 21 and 22 thanks to the progressive screwing action of the driving member 203 and of the reaction of the elastic band 212 which maintains the holding unit 202 in contact against the driving member 203.

In FIG. 23, reference numeral 300 refers to a holding tool of an intracardiac device and which acts as auxiliary for the implantation of the intracardiac device in the heart H (FIG. 1). In the case illustrated in FIG. 23, the tool 300 is coupled with the intracardiac device 101 shown in FIG. 13. The tool 300 extends along an axis A2 and comprises a frame 301 (more clearly visible in FIG. 24), a holding unit 302 for the intracardiac device 101; and a driving member 303 conceived to maintain the holding unit 302 in two operational positions.

In FIG. 24, the frame 301 comprises a plate 304 perpendicular to the axis A2 having a central opening 305 and four slits 306 that terminate in the central opening 305.

The holding unit 302 extends around the bar 304 and comprises a plurality of sectors 308, each one comprising a hub portion 309 and a holding portion 310. Each sector 308 comprises a pin 311, which is engaged in a respective slit 306 and has a holding head 312 as is shown more clearly in FIG. 25.

The intracardiac device 101 as shown in FIG. 23 is fixed to the holding portion by means of suture thread not illustrated in the appended drawings, and under its own elastic force, it pushes the sectors 308 towards the axis A2.

In FIG. 23, the holding portion 310 defines an inner seat 313 to house the elongated member 102.

The holding portion 310 has holes 315 conceived to permit the passage of the suture thread to fix the intracardiac device 101 to the holding portion 310.

In FIG. 24, the hub portion 309 of each sector 308 comprises a tooth 317 which extends towards the axis A2.

Driving member 303 extends along the axis A2 and comprises a prismatic body having four walls 318 that converge towards the axis A2 and two plates 319 and 320 arranged at the opposite ends of the prismatic body. On each wall 318 of the prismatic body are grooves 321 and 322 conceived to house a respective tooth 317. The grooves 321 and 322 define the stable positions of the tool 300: a first position wherein the intracardiac device 101 is arranged in the rest configuration and a position wherein the intracardiac device 101 is arranged in extended configuration.

Method for Implanting the Intracardiac Device in the Heart

The method for implanting the intracardiac device in the heart H (FIG. 1) for restoring functional elasticity of cardiac structures is described with particular reference to the intracardiac device 101 (FIGS. 13 and 14) and to the tool 300 (FIGS. 23-25), which are used for this method. The method comprises the conventional phases associated with an open heart surgery which places the patient in extracorporeal circulation. More specifically, the method of the present invention involves arranging the intracardiac device 101 in an extended configuration (such as that illustrated in FIG. 23) in relation to the rest configuration; and to attaching the intracardiac device 101 in its extended configuration along an internal face of a cardiac structure of the type shown in FIG. 1. Naturally, the tool 300 (FIG. 23) supports the intracardiac device 101 until the intracardiac device 101 is connected to the cardiac structure. Once the intracardiac device 101 has been sutured to the cardiac structure, the connections between the intracardiac device 101 and the tool 300 are cut, and the tool is released and extracted from the heart.

According to an embodiment (not illustrated), the implantation of the intracardiac device is performed by inserting the holding tool, together with the intracardiac device through percutaneous intervention.

A further embodiment (not illustrated) and practicable for implanting the intracardiac device is performed through transapical intervention.

It is obvious that a number of variations can be applied to the embodiments according to the present invention while remaining within the scope of the appended claims.

The invention claimed is:

1. An intracardiac device for restoring functional elasticity of cardiac structures, in particular for the treatment of cardiomyopathies and valvulopathies, storing energy from the cardiac structures and ceding energy to the cardiac structures during the cardiac cycle; wherein the intracardiac device comprises an elongated shape and includes an elongated member formed from metal spring wire; the elongated member being at least partially wound in coils that extend circumferentially, along a given section, and is attachable to a cardiac structure; wherein said coils are selected in material, number, and dimension to permit elastic elongation of the intracardiac device higher than 10% of the rest length of the intracardiac device during use, and are adapted to be exposed to blood flow during use; and wherein the device further comprises at least one member directly attachable to the cardiac structure and attached to the elongated member, and the at least one member has an elongated shape and is arranged alongside and along the elongated member and is extendable up to a maximum length in order to limit extension of the elongated member within a given percentage of the rest length of the elongated member, and the attachable member includes a metal mesh tube intersecting with said coils; the metal mesh tube being extendable.

2. The device according to claim 1, wherein said coils are selected in material, number and dimension to permit elastic elongation of the intracardiac device between 10% and 50% of the rest length of the intracardiac device.

3. The device according to claim 1, wherein said coils are selected in material, number and dimension to permit elastic contraction of the intracardiac device, less than 5% the rest of the length of the intracardiac device.

4. The device according to claim 1, wherein the attachable member is attached to the elongated member leaving said coils at least partially freely exposed to blood flow during use.

5. The device according to claim 1, wherein the elongated member and the attachable member are ring-shaped; each coil of the elongated member being partially embedded in the material of the attachable member.

6. The device according to claim 1, wherein the metal mesh tube forms a closed ring.

7. The device according to claim 1, wherein said coils define at least one helical spring; each coil being set at a distance from the adjacent coil in order to permit elastic compression deformation and elastic traction deformation.

8. The device according to claim 1, wherein the attachable member comprises a support structure realized in a material selected from one of the following:
   Metal; Silicone; Polyurethane; polyethylene terephthalate; ePTFE.

9. The device according to claim 8, wherein the attachable member comprises a composite structure comprising the said support structure and a covering in an attachable material; the covering being realized in a material selected from one of the following:
   polyethylene terephthalate; ePTFE; Pericardial material; Metal.

10. A holding tool of an intracardiac device for restoring functional elasticity of cardiac structures, in particular for the treatment of cardiomyopathies and valvulopathies, storing energy from the cardiac structures and ceding energy to the cardiac structures during the cardiac cycle;
   wherein the device has an elongated shape and comprises an elongated member formed from metal wire for forming springs, at least partially, wound in coils along a given section and attachable to a cardiac wall;
   said coils being selected in material, number, and dimension to permit elastic elongation of the intracardiac device higher than 10% of the rest length of the intracardiac device;
   the holding tool comprising a frame;
   a holding unit mounted in a mobile manner on said frame and having a variable configuration in order to maintain the intracardiac device in the rest configuration and in an extended configuration in relation to the rest configuration; and
   a driving member of the holding unit comprising elements arranged to engage and hold the holding unit respectively in a first stable position to support the intracardiac device in the rest configuration, and in a second stable position to support the intracardiac device in the extended configuration;
   the frame comprising a plate having an aperture formed therein with radial slots extending outwardly from edges of the aperture, and wherein the holding unit comprises a plurality of radially movable segments each including an internal face and an external structure with an undercut area in which the intracardiac device is retained, and wherein the driving member is arranged with a plurality of external surfaces equal to the number of internal faces to progressively move the intracardiac device from its rest configuration into an expanded configuration for suturing into position with the heart, and to then retract the plurality of segments leaving the intracardiac device within the heart in a rest configuration.

11. An intracardiac device for restoring functional elasticity of cardiac structures, in particular for the treatment of cardiomyopathies and valvulopathies, storing energy from the cardiac structures, and ceding energy to the cardiac structures during the cardiac cycle;

wherein the intracardiac device comprises an elongated shape and includes an elongated member formed from metal spring wire; the elongated member being at least partially wound in coils that extend circumferentially, along a given section, and is attachable to a cardiac structure;

wherein said coils are selected in material, number, and dimension to permit elastic elongation of the intracardiac device higher than 10% of the rest length of the intracardiac device during use, and are adapted to be exposed to blood flow during use, and wherein the elongated member is wound in coils on a plurality of sections to form a plurality of helical springs;

the device further comprising a plurality of attachable members, which are attached to the elongated member, alternates with the helical springs, and encase the elongated member at least partially.

12. The device according to claim 11, wherein the said coils are selected in material, number, and dimension to permit elastic elongation of the intracardiac device between 10% and 50% of the rest length of the intracardiac device.

13. The device according to claim 11, wherein the said coils are selected in material, number, and dimension to permit elastic elongation of the intracardiac device less than 5% of the rest length of the intracardiac device.

14. The device according to claim 11, wherein the attachable member includes a metal mesh tube intersecting with said coils; the metal mesh tube being extendable.

15. The device according to claim 11, wherein the plurality of attachable members are attached to one another.

16. The device according to claim 11, wherein the attachable member comprises a support structure realized in a material selected from one of the following:

Metal; Polyethylene terephthalate; ePTFE; Pericardial material.

17. The device according to claim 16, wherein the attachable member comprises a composite structure comprising the said support structure and a covering in an attachable material; the covering being realized in a material selected from one of the following:

Metal; Silicone; Polyurethane; Polyethylene terephthalate; ePTFE.

18. An intracardiac device for restoring functional elasticity of cardiac structures, in particular for the treatment of cardiomyopathies and valvulopathies, by storing energy from the cardiac structures and ceding energy to the cardiac structures during the cardiac cycle;

the intracardiac device comprising an elongated shape and including an elongated member formed from metal spring wire; the elongated member being at least partially wound in coils that extend along a given section and being attachable to a cardiac structure;

wherein said coils are selected in material, number, and dimension to permit elastic elongation of the intracardiac device higher than 10% of the rest length of the intracardiac device during use, and are adapted to be exposed to blood flow during use; and wherein the device further comprises at least one member directly attachable to the cardiac structure and attached to the elongated member, the at least one member has an elongated shape and is arranged alongside and along the elongated member and is extendable up to a maximum length in order to limit extension of the elongated member within a given percentage of the rest length of the elongated member, and the attachable member includes a metal mesh tube intersecting with said coils; the metal mesh tube being extendable.

19. The device as in claim 18 wherein the coils are inserted in the mesh of the tube in order to join the metal mesh tube to the elongated structure.

* * * * *